US008500785B2

(12) United States Patent
Gunderson

(10) Patent No.: US 8,500,785 B2
(45) Date of Patent: Aug. 6, 2013

(54) CATHETER

(75) Inventor: Richard C. Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 834 days.

(21) Appl. No.: 10/890,082

(22) Filed: Jul. 13, 2004

(65) Prior Publication Data

US 2006/0015168 A1    Jan. 19, 2006

(51) Int. Cl.
*A61F 2/06*    (2006.01)

(52) U.S. Cl.
USPC .................................. 623/1.11; 604/523

(58) Field of Classification Search
USPC ... 623/1.11, 1.12, 1.22; 606/108; 604/103.09, 604/523, 524, 525, 526, 527; 600/435; 264/171.4, 171.16, 171.14, 171.18, 174.18
See application file for complete search history.

(56) References Cited

U.S. PATENT DOCUMENTS

| | | | |
|---|---|---|---|
| 3,879,516 A * | 4/1975 | Wolvek | 264/135 |
| 4,530,855 A | 7/1985 | Youngkeit | |
| 4,861,621 A | 8/1989 | Kanzaki | |
| 4,862,922 A | 9/1989 | Kite, III | |
| 5,335,167 A | 8/1994 | Boyd | |
| 5,571,168 A | 11/1996 | Toro | |
| 5,601,599 A | 2/1997 | Nunez | |
| 5,607,531 A | 3/1997 | Needham et al. | |
| 5,614,139 A | 3/1997 | Cutolo et al. | |
| 5,662,675 A | 9/1997 | Polanskyj Stockert et al. | |
| 5,733,267 A | 3/1998 | Del Toro | |
| 5,772,668 A * | 6/1998 | Summers et al. | 623/1.11 |
| 5,788,707 A | 8/1998 | Del Toro et al. | |
| 5,879,342 A * | 3/1999 | Kelley | 600/524 |
| 5,951,539 A * | 9/1999 | Nita et al. | 604/526 |
| 6,053,903 A | 4/2000 | Samson et al. | |
| 6,068,634 A | 5/2000 | Lorentzen et al. | |
| 6,096,045 A | 8/2000 | Del Toro et al. | |
| 6,159,187 A * | 12/2000 | Park et al. | 604/264 |
| 6,342,066 B1 | 1/2002 | Toro et al. | |
| 6,368,344 B1 * | 4/2002 | Fitz | 623/1.11 |
| 6,413,269 B1 * | 7/2002 | Bui et al. | 623/1.11 |
| 6,443,926 B1 * | 9/2002 | Kletschka | 604/96.01 |
| 6,468,298 B1 | 10/2002 | Pelton | |
| 6,508,825 B1 | 1/2003 | Selmon et al. | |
| 6,511,462 B1 * | 1/2003 | Itou et al. | 604/264 |
| 6,527,752 B1 * | 3/2003 | Bosley et al. | 604/264 |
| 6,589,227 B2 | 7/2003 | Sonderskov Klint | |

(Continued)

FOREIGN PATENT DOCUMENTS

| | | |
|---|---|---|
| EP | 1 120 127 | 8/2004 |
| WO | WO 01/47436 | 7/2001 |
| WO | WO 2004/096091 | 11/2004 |

OTHER PUBLICATIONS

International Search Report, PCT/US2005/024737, dated Feb. 13, 2006.

(Continued)

*Primary Examiner* — Victor Nguyen
(74) *Attorney, Agent, or Firm* — Seager, Tufte & Wickhem LLC

(57) ABSTRACT

A catheter including a tube and a coil at least partially surrounding the tube is disclosed. The coil can include a first portion including a first material, and a second portion including a second material.

20 Claims, 4 Drawing Sheets

U.S. PATENT DOCUMENTS

| | | |
|---|---|---|
| 6,623,491 B2 | 9/2003 | Thompson |
| 6,669,886 B1 | 12/2003 | Willard |
| 6,702,843 B1 * | 3/2004 | Brown et al. ............... 623/1.11 |
| 6,773,446 B1 | 8/2004 | Dwyer et al. |
| 7,037,290 B2 * | 5/2006 | Gardeski et al. ........... 604/95.01 |
| 7,041,125 B2 * | 5/2006 | Hwang et al. ............... 623/1.11 |
| 2002/0095203 A1 | 7/2002 | Thompson et al. |
| 2003/0014044 A1 * | 1/2003 | Krishnan et al. ............... 606/41 |
| 2004/0002727 A1 | 1/2004 | Hwang et al. |
| 2004/0002728 A1 * | 1/2004 | Speck et al. ................. 606/194 |
| 2004/0078071 A1 * | 4/2004 | Escamilla et al. ........... 623/1.11 |
| 2004/0097959 A1 | 5/2004 | Thompson |
| 2004/0148000 A1 * | 7/2004 | Bilge .......................... 623/1.11 |
| 2005/0065474 A1 | 3/2005 | Larson et al. |

OTHER PUBLICATIONS

Schetsky, L. McDonald, "Shape Memory Alloys", Encyclopedia of Chemical Technology (3rd edition) John Wiley & Sons, 1982, vol. 20 pp. 726-736.

* cited by examiner

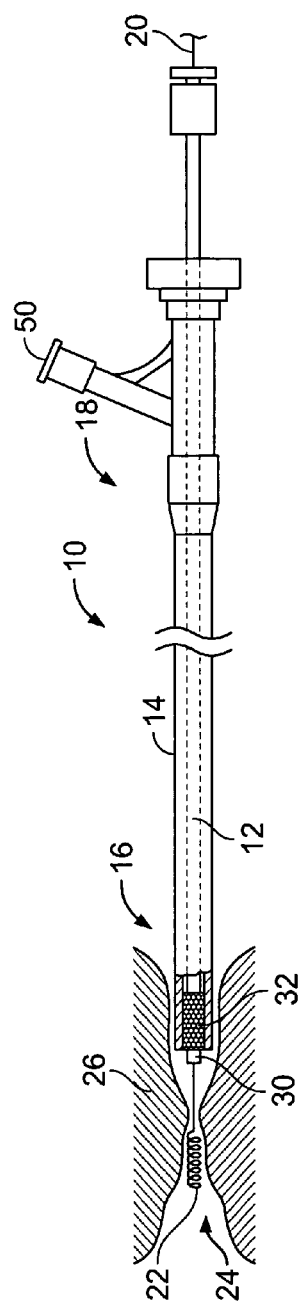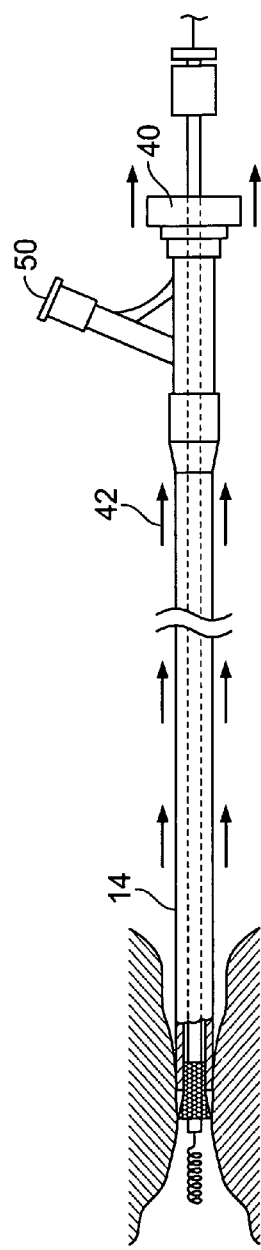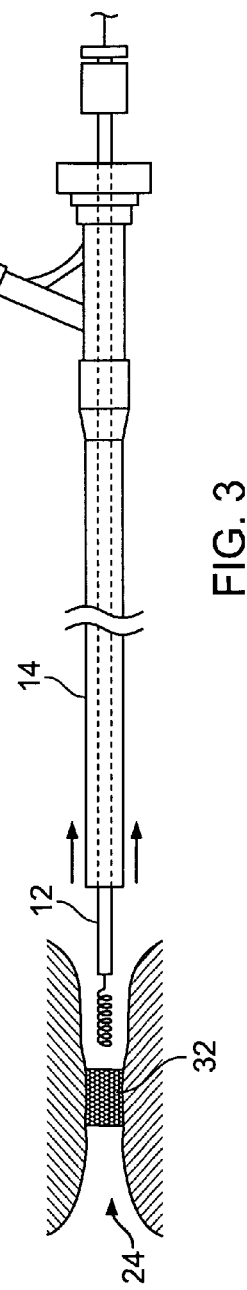
FIG. 1
FIG. 2
FIG. 3

CATHETER

TECHNICAL FIELD

This invention relates to catheters, as well as related systems and methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include a sheath surrounding a catheter with a stent positioned therebetween. Generally, the operator of the system positions the distal portion within the lumen at a desired location (e.g., so that the stent is adjacent an occlusion). The operator can then retract the sheath to allow the stent to engage the occlusion/lumen wall. Thereafter, the operator removes the distal portion of the system from the lumen.

SUMMARY

In general, the invention relates to catheters, as well as related systems and methods. The catheters can be used, for example, in implantable medical endoprosthesis delivery systems (e.g., stent delivery systems). The systems can be used, for example, to deliver a medical endoprosthesis (e.g., a stent) at a desired location within a lumen of a subject (e.g., an artery of a human).

The catheters generally include a tube and a coil that at least partially surrounds the tube. In some embodiments, the coil can include a first portion disposed inwardly of a second portion, where the first and second portions are made of different materials. For example, the first portion of the coil can be in the form of a wire (e.g., a wire formed of a metal or alloy), and the second portion of the coil can be a polymer (e.g., a thermoplastic) coated on the wire. In certain embodiments, the tube and coil can be at least partially surrounded by a sheath (e.g., a sheath that is heat shrunk to the exposed surfaces of the tube and coil).

The catheters can be sufficiently flexible for use in implantable medical endoprosthesis delivery systems while also having a relatively high compression resistance. This can, for example, allow the catheters to undergo little or no compression or buckling during deployment of a medical endoprosthesis (e.g., stent), which can enhance the precision of placement of the medical endoprosthesis (e.g., stent) during deployment.

Alternatively or additionally, the catheters can be designed to allow good fluid flow between the catheter and a surrounding sheath, which can aid in delivery of the system to a desired site within a subject (e.g., a human) and/or deployment of the medical endoprosthesis (e.g., stent) at a desired site (e.g., an artery of a human).

Other features and advantages of the invention will be apparent from the description, drawings and claims.

DESCRIPTION OF DRAWINGS

FIGS. 1-3 are side views of an embodiment of an endoprosthesis delivery system during use.

Like reference symbols in the various drawings indicate like elements.

DETAILED DESCRIPTION

Figure 4:
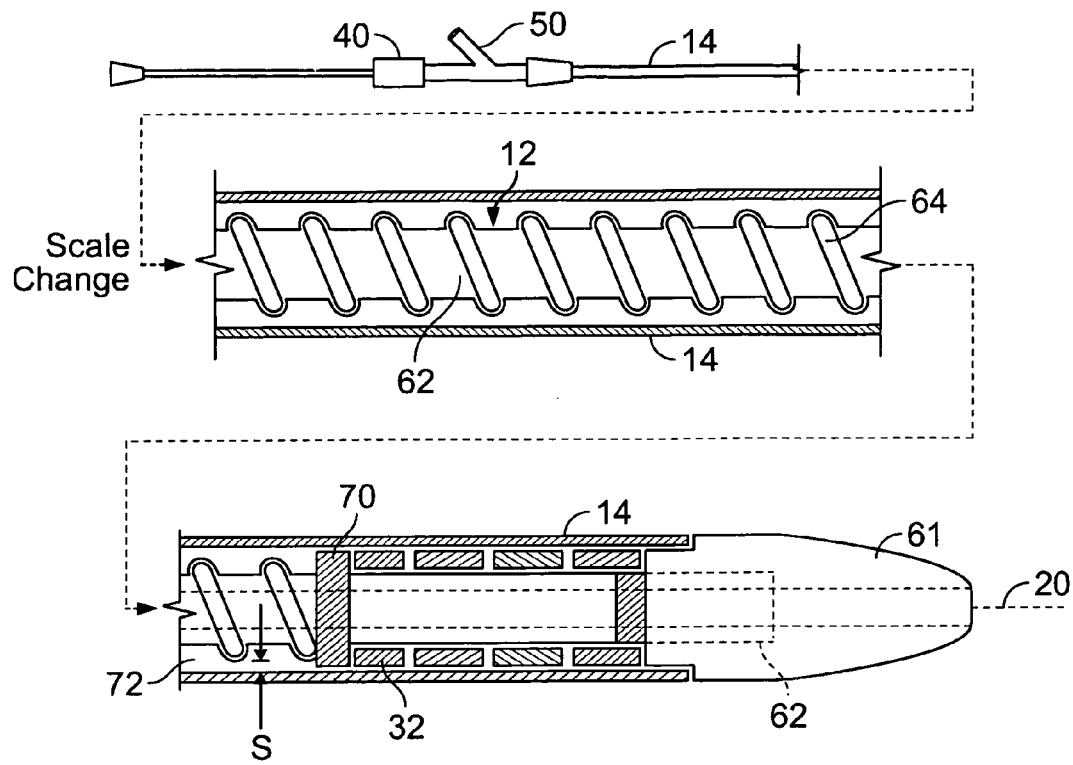
FIG. 4. is an exploded, mixed view of an embodiment of an endoprosthesis delivery system.

FIGS. 1-3 show an implantable medical endoprosthesis delivery system 10 that includes a catheter 12, a sheath 14 surrounding catheter 12, and a stent 32 positioned between catheter 12 and sheath 14. The delivery system 10 includes a distal end 16 dimensioned for insertion into a body lumen (e.g., an artery of a human) and a proximal end 18 that resides outside the body of a subject, and that contains at least one port 50 and lumens for manipulation by a physician. A guide wire 20 with a blunted end 22 is inserted into a body lumen 24 by, for example, making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, catheter 12, stent 32 and sheath 14 are placed over the proximal end of guide wire 20. Catheter 12, stent 32 and sheath 14 are moved distally over guide wire 20 and positioned within lumen 24 so that stent 32 is adjacent constricted site 26 of lumen 24. Sheath 14 is moved proximally, allowing stent 32 to expand and engage constricted site 26. Sheath 14, catheter 12 and guide wire 20 are removed from body lumen 24, leaving stent 32 engaged with constricted site 26.

Figure 5A:
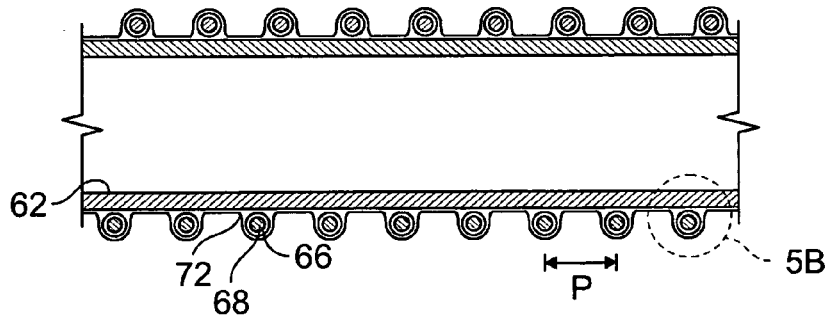
FIG. 5A is an axial cross-sectional view of the catheter shown in FIG. 4, area B.
Figure 5B:
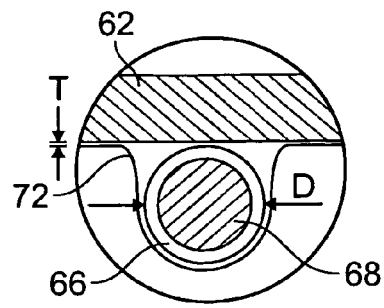
FIG. 5B is an enlarged view of area 5B shown in FIG. 5A.
Figure 6:
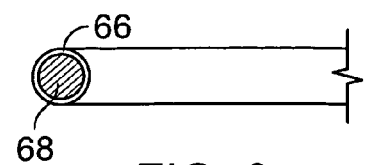
FIG. 6 is a perspective view of a portion of an embodiment of a coil, illustrating first and second portions.

As shown in FIGS. 4-6, catheter 12 includes a tube 62 surrounded by a coil 64. Catheter 12 also includes a coating 72 that surrounds tube 62 and coil 64. Catheter 12 is dimensioned so that a space, S, is present between catheter 12 and sheath 14 (see FIG. 4, area C). Without wishing to be bound by theory, it is believed that with this configuration catheter 12 can exhibit enhanced compression resistance with little or no buckling of catheter 12 (e.g., as sheath 14 is retracted proximally). It is also believed that this configuration also allows for appropriate fluid flow between catheter 12 and sheath 14.

Coil 64 includes an inner portion 68 that is surrounded by an outer portion 66. Inner portion 68 can be, for example, a wire formed of a metal, an alloy or a polymeric material. Examples of metals include platinum and gold. Examples of alloys include gold-containing alloys, platinum-containing alloys, stainless steel and shape memory alloys. Examples of shape memory alloys include nitinol, silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium ($Fe_3Be$), iron platinum ($Fe_3Pt$), indium-thallium (In—Tl), iron-manganese (Fe—Mn), nickel-titanium-vanadium (Ni—Ti—V), iron-nickel-titanium-cobalt (Fe—Ni—Ti—Co) and copper-tin (Cu—Sn). For yet additional shape memory alloys, see, for example, Schetsky, L. McDonald, "Shape Memory Alloys", *Encyclopedia of Chemical Technology* (3rd ed.), John Wiley & Sons, 1982, vol. 20. pp. 726-736. Examples of polymeric materials include nylons, thermoplastic polyester elastomers (e.g., Hytrel®), copolyester elastomers (e.g., Amitel® copolyester elastomers), polyether-block co-polyamide polymers (e.g., PEBAX®) and high-density polyethylene (HDPEs).

Outer portion 66 can be, for example, a polymeric material, such as a plastic (e.g., a thermoplastic). Examples of polymeric materials include polyamides, polyurethanes, styrenic block copolymers, nylons, thermoplastic polyester elastomers (e.g., Hytrel®), copolyester elastomers (e.g., Arnitel® copolyester elastomers), polyether-block co-polyamide polymers (e.g., PEBAX®) and HDPEs. In some embodiments, outer portion 66 is integral with the outer surface of tube 62. This can, for example, assist in maintaining the position of coil 64 constant with respect to tube 62.

In some embodiments, coil 64 is a helical coil with a pitch, P, (see FIG. 5A) between adjacent windings of, for example, from at least about 0.005 inch (e.g., at least about 0.01 inch, at least about 0.05 inch) and/or at most about 0.1 inch (e.g., at most about 0.075 inch, at most about 0.06 inch). In certain embodiments, the pitch P of coil 64 is from about 0.005 inch to about 0.1 (e.g., from about 0.01 inch to about 0.06 inch, from about 0.05 inch to about 0.06 inch). In some embodiments, coil 64 is circular in cross-section with a diameter, D, (see FIG. 5B) of at least about 0.002 inch (e.g., at least about 0.004 inch) and/or at most about 0.01 (e.g., at most about 0.005 inch). For example, in certain embodiments, the diameter, D, of coil 64 can be from about 0.002 inch to about 0.1 inch (e.g., from about 0.004 inch to about 0.006 inch, about 0.005 inch).

In general, coating 72 is made of a material that can be bonded to the exposed outer surfaces of tube 62 and coil 64. Examples of such materials include heat shrink materials and polymeric materials such as polyether-block co-polyamide polymers (e.g., PEBAX®) and nylons. Examples of heat shrink materials include cross-linked polyethylene, polyester (e.g., PET) heat shrink, fluorinated ethylene (FEP) heat shrink, polytetrafluoroethylene (PTFE) heat shrink. In some embodiments, coating 72 includes an additive (e.g., a fluoropolymer, a silicone, an ultrahigh molecular weight polyethylene, an oil, or blends thereof) to assist in the movement of catheter 12 with respect to sheath 14 and stent 32. In certain embodiments, the thickness, T, of coating 72 (see FIG. 5B) is at least about 0.001 inch (e.g., at least about 0.002 inch) and/or at most about 0.01 inch (e.g., at most about 0.008 inch). In some embodiments, the thickness, T, of coating 72 is from about 0.001 inch to about 0.01 inch (e.g., from about 0.002 inch to about 0.008 inch, about 0.006 inch).

Stent 32 is typically formed of a shape memory alloy. Examples of shape memory alloys include those discussed above with respect to inner portion 68 of coil 64.

In general, tube 62 is made of a polymeric material. Examples of polymeric materials include polyether-block co-polyamide polymers (e.g., PEBAX®), copolyester elastomers (e.g., Amitel® copolyester elastomers), thermoplastic polyester elastomers (e.g., Hytrel®), thermoplastic polyurethane elastomers (e.g., Pellethane™), polyolefins (e.g., Marlex® polyethylene, Marlex® polypropylene), HDPEs, low-density polyethylenes (LDPEs), polyamides (e.g., Vestamid®), and combinations of these materials.

Typically, sheath 14 is made of a polymeric material. Examples of polymeric materials include those noted above with respect to tube 62. In some embodiments, sheath 14 includes an additive (e.g., a fluoropolymer, a silicone, an ultrahigh molecular weight polyethylene, an oil, or blends thereof) to assist in the movement of sheath 14 with respect to catheter 12 and stent 32.

FIG. 4 shows that system 10 can further include a bumper 70 that is integral with tube 62, and a tip 61 that is integral with tube 62. Bumper 70 can reduce the possibility of stent 32 moving proximally as sheath 14 is retracted proximally, and tip 61 can assist in positioning of system 10 within body lumen 26 (e.g., as system 10 is moved distally over guide wire 20 within body lumen 24). In some embodiments, bumper 70 is formed of a polymeric material, such as a polyether-block co-polyamide polymer (e.g., PEBAX®) or a thermoplastic polyurethane elastomer (e.g., Pellethane™). In certain embodiments, bumper 70 is made of a metal or an alloy, such as, for example, stainless steel, Nitinol and/or platinum. Tip 61 is typically formed of a relatively soft polymeric material.

In general, catheter 12 can be prepared as desired. In some embodiments, catheter 12 can be prepared as follows.

Figure 7:
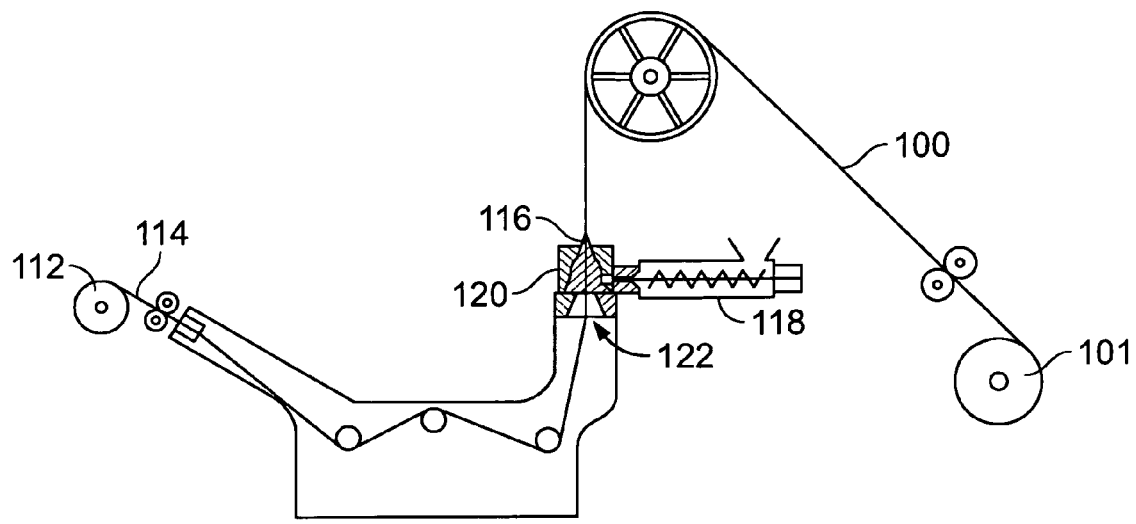
FIG. 7 is a schematic view illustrating a portion of an embodiment of a process for forming a coil.

A monofilament having a transverse cross-section similar to that of coil 64 is prepared. FIG. 7 illustrates an embodiment of a pultrusion process for a making a monofilament 100. A spool 112 of a metallic filament (e.g., stainless steel wire) 114 is pulled through a fluid polymeric material (e.g., molten thermoplastic) 116 that is pumped onto filament 114 by extruder 118 as filament 114 passes through a die 120 with an aperture 122. After exiting die 120, monofilament 100 is collected on a spool 101. Pultrusion processes are disclosed, for example, in U.S. Pat. Nos. 4,530,855, 4,861,621, 4,862, 922, 5,607,531 and 5,614,139. Equipment for performing pultrusion processes is commercially available from, for example, Entec Composite Machines, Salt Lake City, Utah (USA) and Pultrex, Essex (UK).

Figure 9:
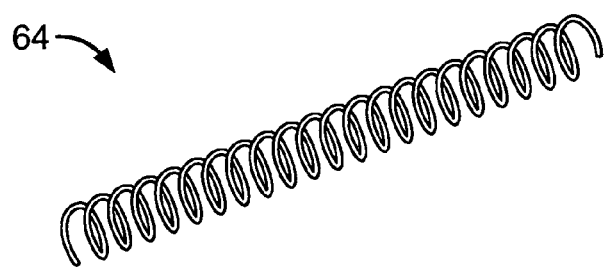
FIG. 9 is a perspective view of an embodiment of a coil.
Figure 8:
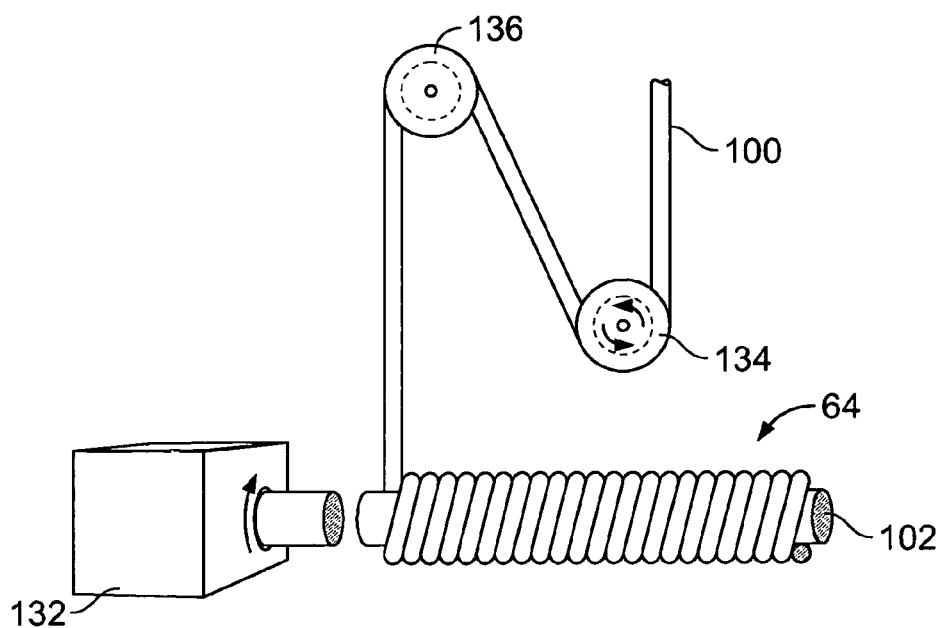
FIG. 8 is a schematic view, illustrating a portion of an embodiment of a process for forming a coil.

Monofilament 100 is formed into a coil. FIG. 8 shows an embodiment of a process for forming monofilament 100 into a coil by winding monofilament 100 around a mandrel 102 as mandrel 102 is rotated by a motor 132. Monofilament 100 is supplied to mandrel 102 via a main tension pulley 134 and a cantilevered pulley 136. Generally, mandrel 102 is several inches (e.g., about two inches) longer than the desired coil length. Filament winding processes are disclosed, for example, in U.S. Pat. Nos. 5,335,167 and 5,601,599. Filament winding equipment is commercially available from, for example, Pultrex, Essex (UK). Wound monofilament 100 is removed from mandrel 102 to provide coil 64 (see FIG. 9).

Figure 10:
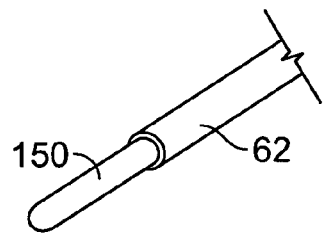
FIG. 10 is a perspective view of an embodiment of a portion of a process for making a catheter.

Tube 62 is placed around a support member, then coil 64 is placed around tube 62, and wound filament 100 is made integral with tube 62, thereby providing tube 62 surrounded by coil 64 (see discussion above). FIG. 10 shows tube 62 disposed around a support member 150. Support member 150 reduces the possibility of tube 62 being deformed during subsequent processing. After being positioned around tube 62, coil 64 can be made integral with tube 62 by exposure to energy (e.g., heat, UV, IR). In some embodiments, outer material 66 of coil 64 is a thermoplastic material, and coil 64 can be made integral with tube 62 by heating outer material 66 with a heat gun so that outer material 66 is welded to tube 62.

Figure 11:
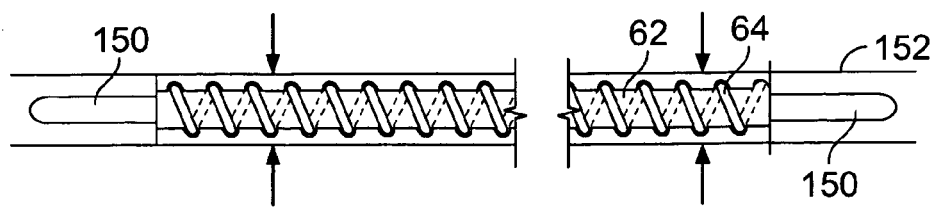
FIG. 11 is a side view of an embodiment of a portion of a process for making a catheter.

A coating material is placed around tube 62 and coil 64, and the coating material is processed to form coating 72 (see discussion above). FIG. 11 shows an embodiment in which a heat shrink tubing 152 is disposed around tube 62 and coil 64. Tubing 152 is then exposed to radiation (e.g., heat, UV, IR) to collapse tubing 152 and adhere it to the exposed outer surfaces of tube 62 and coil 64, thereby forming coating 72.

While certain embodiments have been described, other embodiments are possible.

As an example, while systems including a self-expanding stent have been described, other types of implantable medical endoprostheses can be used in the systems. For example, the implantable medical endoprosthesis can be a balloon-expandable implantable medical endoprostheses (e.g., a balloon-expandable stent). In such systems, inner catheter 12 would typically include an expandable balloon in the region around which the implantable medical endoprostheses is exposed during delivery. Additional examples of implantable medical endoprostheses include stent-grafts and filters (e.g., arterial filters, venus filters).

As another example, while embodiments of catheter 12 have been described in which catheter 12 includes coating 72, in some embodiments catheter 12 does not include coating 72.

As an additional example, while embodiments of catheter 12 have been described in which coil 64 is formed of two different (inner and outer) layers, in certain embodiments coil 64 may be formed of a single portion, or coil 64 may be formed of more than two portions (e.g., three layers, four layers, five layers, six layers, seven layers, eight layers, nine layers, 10 layers). Optionally, the portions can be in the shape of layers.

As a further example, while embodiments have been described in which coil 64 has a circular transverse cross-section, in some embodiments coil 64 can have a noncircular transverse cross-section (e.g., half moon shaped transverse cross-section, rectangular transverse cross-section, hexagonal transverse cross-section, pentagonal transverse cross-section, octagonal transverse cross-section). This can be achieved, for example, by using a correspondingly shaped inner portion (e.g., a correspondingly shaped wire). As an example, in embodiments in which inner portion 68 has a rectangular transverse cross-section, the width of the transverse cross-section of inner portion 68 can be, for example, at least about 0.001 inch (e.g., at least about 0.004 inch) and/or at most about 0.01 inch (e.g., at most about 0.008 inch), and the length of the transverse cross-section of inner portion 68 can be, for example, at least about 0.001 inch (e.g., at least about 0.004 inch) and/or at most about 0.05 inch (e.g., at most about 0.03 inch). As another example, in embodiments in which inner portion 68 has a half-moon transverse cross-section, the transverse cross-section of inner portion 68 can be at least about 0.001 inch (e.g., at least about 0.004 inch) and/or at most about 0.03 inch (e.g., at most about 0.01 inch), and the orthogonal dimension of the transverse cross-section of inner portion 68 can be at least about 0.001 inch (e.g., at least about 0.003 inch) and/or at most about 0.01 inch (e.g., at most about 0.008 inch).

As another example, in some embodiments, coating 72 is created by a pultrusion process.

As an additional example, while embodiments have been described in which there is a space between catheter 12 and sheath 14, in some embodiments catheter 12 and sheath 14 are dimensioned so that they are in contact. In such embodiments, fluid flow between catheter 12 and sheath 14 can be achieved, for example, along coil 64.

As a further example, in some embodiments wire 114 is drawn through a resin bath rather than die 120. In certain embodiments (e.g., to toughen the outer portion of the monofilament), the resin (e.g., a thermoset) can be cured by heat. Optionally, additional materials (e.g., pigments, curing accelerators, fillers, release agents) can be added to the outer portion of monofilament 100.

As another example, while embodiments have been described in which coil 64 has a constant pitch, in certain embodiments, the pitch of coil 64 can vary, or coil 64 can include regions in which the pitch varies. For example, coil 64 can have a first region in which coil 64 has a constant pitch, and coil 64 can have a second region in which coil 64 has a constant pitch that is different from the pitch in the first region of coil 64.

As an additional example, in some embodiments coil 64 surrounds only a portion of tube 62.

As a further example, multiple coils can surround tube 62. For example, each coil can surround a different region of tube 62.

Other embodiments are in the claims.

What is claimed is:

1. A catheter, comprising:
    a tube comprising a material, the tube having an inner surface and an outer surface;
    a bumper extending radially from the tube for restricting proximal movement of a stent positioned on the tube and distal to the bumper;
    a coil at least partially surrounding the tube,
    wherein:
        the coil includes a first portion comprising a first material,
        the coil includes a second portion comprising a second material different from the first material,
        the first portion of the coil is in the form of a coating that surrounds the second portion of the coil, a portion of the coating being disposed between the second portion and the outer surface of the tube;
        the coil is proximal to the bumper;
        the coil defines an uneven outer surface of the catheter including a helical ridge
        the coil is an open-pitch coil having a space between adjacent windings, and
    the catheter is configured so that it can be used as an inner catheter in an implantable medical endoprosthesis delivery system; and
    a coating surrounding at least a portion of the tube and the coil along an axial length of the catheter.

2. The catheter of claim 1, wherein the coil is integral with the outer surface of the tube.

3. The catheter of claim 1, wherein the coil is helically wrapped around the tube.

4. The catheter of claim 1, wherein the first material comprises a polymer.

5. The catheter of claim 4, wherein the polymer is selected from the group consisting of polyamides, polyurethanes, styrenic block copolymers, and mixtures thereof 6. The catheter of claim 1, wherein the second material comprises a metal or alloy.

7. The catheter of claim 6, wherein the second material is selected from the group consisting of stainless steel, shape memory alloys, platinum, gold and combinations thereof 8. The catheter of claim 1, wherein the coating surrounding at least a portion of the tube and the coil directly contacts the outer surface of the tube and an exposed surface of the coil.

9. The catheter of claim 1, wherein the coating surrounding at least a portion of the tube and the coil is a heat shrink coating.

10. A catheter, comprising:
    a tube comprising a material, the tube having an inner surface and an outer surface;
    a bumper extending radially from the tube for restricting proximal movement of a stent positioned on the tube and distal to the bumper;
    an open-pitch coil at least partially surrounding the tube and the open-pitch coil abutting a proximal side of the bumper, the coil comprising a metallic filament and a polymeric material disposed on the metallic filament, some of the polymeric material being disposed between the metallic filament and the outer surface of the tube; and a coating at least partially surrounding the tube and the coil, wherein the coil is proximal to the bumper, wherein the coil defines an outer surface of the catheter and defines a space between the catheter and a sheath that is configured to allow for fluid flow between the catheter and the sheath, and the catheter is configured so that it can be used as the inner catheter in an implantable medical endoprosthesis delivery system.

11. The catheter of claim 10, wherein the coating directly contacts the outer surface of the tube and an exposed surface of the coil.

12. The catheter of claim 10, wherein the coating is a heat shrink coating.

13. The catheter of claim 10, wherein the coating comprises a polymer selected from the group consisting of polyesters, FEPs and PTFEs.

14. The catheter of claim 10, wherein the coil is integral with the outer surface of the tube.

15. The catheter of claim 10, wherein the coil is helically wrapped around the tube.

16. The catheter of claim 10, wherein the polymeric material surrounds the metallic filament.

17. An implantable medical endoprosthesis delivery system, comprising:
   a catheter, comprising:
      a tube comprising a material, the tube having an inner surface and an outer surface;
      a bumper extending radially from the tube for restricting proximal movement of a stent positioned on the tube and distal to the bumper;
      an open-pitch coil disposed on the outer surface of the tube and at least partially surrounding the tube, the coil including a first portion comprising a first material and a second portion comprising a second material different from the first material, the second portion of the coil being disposed inwardly of the first portion of the coil, part of the first portion being disposed between the second portion and the outer surface of the tube; and
      a coating at least partially surrounding the tube and the coil; and
   a sheath at least partially surrounding the catheter,
   wherein the coil is proximal to the bumper and abuts a proximal end of the bumper and provides compression resistance, the coil defines an outer surface of the catheter and defines a space between the catheter and the sheath that is configured to allow for fluid flow between the catheter and the sheath, and the catheter and the sheath are configured so that an implantable medical endoprosthesis can be disposed therebetween.

18. The implantable medical endoprosthesis delivery system of claim 17, further comprising the implantable medical endoprosthesis between the catheter and the sheath.

19. A method of treating a lumen within a patient, the method comprising:
   inserting the system of claim 18 in the lumen; and
   expanding the endoprosthesis.

20. The implantable medical endoprosthesis system of claim 17, wherein the first portion of the coil is in the form of a coating that surrounds the second portion of the coil.

* * * * *